United States Patent
Minagawa (10) Patent No.: US 10,088,050 B2
(45) Date of Patent: Oct. 2, 2018

(54) GASKET

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 566 days.

(21) Appl. No.: 14/790,229

(22) Filed: Jul. 2, 2015

(65) Prior Publication Data

US 2016/0033042 A1 Feb. 4, 2016

(30) Foreign Application Priority Data

Jul. 31, 2014 (JP) .................... 2014-156611

(51) Int. Cl.
| F16J 15/10 | (2006.01) |
| A61M 5/315 | (2006.01) |
| F16J 1/00 | (2006.01) |
| C10M 107/42 | (2006.01) |

(52) U.S. Cl.
CPC ........ *F16J 15/102* (2013.01); *A61M 5/31513* (2013.01); *C10M 107/42* (2013.01); *F16J 1/003* (2013.01); *F16J 15/104* (2013.01); *F16J 15/108* (2013.01)

(58) Field of Classification Search
None
See application file for complete search history.

(56) References Cited

U.S. PATENT DOCUMENTS

| 2012/0016314 A1 | 1/2012 | Tachikawa et al. |
| 2015/0203612 A1* | 7/2015 | Minagawa ............... C08F 2/50 522/46 |

FOREIGN PATENT DOCUMENTS

| JP | 2004-298220 A | 10/2004 | |
| JP | WO 2009128265 A1 * | 10/2009 | ........ A61M 5/31513 |
| JP | 2010-142573 A | 7/2010 | |
| JP | WO 2014038688 A1 * | 3/2014 | ................ C08F 2/50 |
| WO | WO 2009/128265 A1 | 10/2009 | |
| WO | WO 2010/103919 A1 | 9/2010 | |
| WO | WO 2014/038688 A1 | 3/2014 | |

OTHER PUBLICATIONS

Machine translation of WO2009128265 retrieved on Nov. 13, 2017.*
Full Machine translation, for JP-2004-298220-A, dated Oct. 28, 2004.
Full Machine translation, for JP-2010-142573-A, dated Jul. 1, 2010.

* cited by examiner

*Primary Examiner* — Christopher M Polley
(74) *Attorney, Agent, or Firm* — Birch, Stewart, Kolasch & Birch, LLP (57) ABSTRACT

The present invention provides a gasket excellent in properties such as sliding properties and resistance to liquid leakage. The present invention relates to a gasket whose sliding surface includes annular projections, the gasket having polymer chains immobilized on at least part of its surface, the annular projections including a first projection that is nearest to a top face, and a bottom side projection that is farthest from the top face, the first projection and/or the bottom side projection having an annular flat portion with a width of 0.1 mm or more.

14 Claims, 1 Drawing Sheet

GASKET

TECHNICAL FIELD

The present invention relates to a gasket.

BACKGROUND ART

In view of the importance of resistance to liquid leakage, elastic bodies such as rubber are used in parts which slide while maintaining a seal, e.g., a gasket which is integrated with a plunger of a syringe and forms a seal between the plunger and the barrel. Unfortunately, such elastic bodies have a slight problem with the sliding properties (see Patent Literature 1). To address this problem, a sliding property improving agent, for example silicone oil, is applied to the sliding surface; however, a concern has been raised over the potential adverse effects of silicone oil on recently marketed bio-preparations. On the other hand, gaskets not coated with a sliding property improving agent have poor sliding properties and therefore do not allow plungers to be smoothly pushed but cause them to pulsate during administration, resulting in problems such as inaccurate injection amounts and infliction of pain on patients.

To satisfy the conflicting requirements, that is, resistance to liquid leakage and sliding properties, a method of coating surfaces with a self-lubricating PTFE film has been proposed (see Patent Literature 2). Unfortunately, such PTFE films are generally expensive and increase the production cost of processed products, limiting the range of application of the method. Also, products coated with PTFE films might not be reliable when they are used in applications where sliding or the like is repeated and durability is therefore required. Furthermore, since PTFE is vulnerable to radiation, PTFE-coated products unfortunately cannot be sterilized by radiation.

CITATION LIST

Patent Literature

Patent Literature 1: JP 2004-298220 A
Patent Literature 2: JP 2010-142573 A

SUMMARY OF INVENTION

Technical Problem

The present invention aims to solve the above problems and provide a gasket excellent in properties such as sliding properties and resistance to liquid leakage.

Solution to Problem

The present invention relates to a gasket whose sliding surface includes annular projections, the gasket having polymer chains immobilized on at least part of its surface,
the annular projections including a first projection that is nearest to a top face and a bottom side projection that is farthest from the top face,
at least one of the first projection or the bottom side projection having an annular flat portion with a width of 0.1 mm or more.

Preferably, the bottom side projection has an annular flat portion which is wider than that of the first projection.

Preferably, the bottom side projection has an annular flat portion with a width of 0.4 mm or more.

Preferably, the gasket includes three or more annular projections,
the annular projections include an intermediate projection between the first projection and the bottom side projection, and
the intermediate projection has a smaller outer diameter than the first projection and the bottom side projection.

Preferably, the outer diameter of the intermediate projection is 96 to 99.5% of the outer diameter of the first projection.

Preferably, a curved surface portion is provided on top and bottom sides of the first projection, and
the curved surface portion on the bottom side has a greater curvature than the curved surface portion on the top side.

Preferably, the curved surface portion on the bottom side has a curvature of 0.4 to 2.0.

Preferably, the polymer chains are immobilized by a surface modification method including:
step 1 of forming polymerization initiation points A on a surface of a gasket base material; and
step 2 of radically polymerizing a monomer, starting from the polymerization initiation points A, to grow polymer chains.

Preferably, the surface modification method includes
step 3 of further extending the polymer chains grown in the step 2, or immobilizing different polymer chains onto the polymer chains grown in the step 2.

Preferably, the step 1 includes adsorbing a photopolymerization initiator A onto a surface of a gasket base material, optionally followed by irradiation with LED light having a wavelength of 300 to 450 nm, to form polymerization initiation points A from the photopolymerization initiator A on the surface.

Preferably, the step 2 includes radically polymerizing a monomer, starting from the polymerization initiation points A, by irradiation with LED light having a wavelength of 300 to 450 nm to grow polymer chains.

Preferably, the polymer chains are immobilized by a surface modification method including
step I of radically polymerizing a monomer in the presence of a photopolymerization initiator A on a surface of a gasket base material to grow polymer chains.

Preferably, the surface modification method includes
step II of further extending the polymer chains grown in the step I, or immobilizing different polymer chains onto the polymer chains grown in the step I.

Preferably, the step I includes radically polymerizing a monomer by irradiation with LED light having a wavelength of 300 to 450 nm to grow polymer chains.

Preferably, a length of the polymer chain is 10 to 50000 nm.

Advantageous Effects of Invention

In the gasket of the present invention, the sliding surface of the gasket includes annular projections, and the gasket has polymer chains immobilized on at least part of its surface, wherein the annular projections include a first projection that is nearest to the top face, and a bottom side projection that is farthest from the top face, and the first projection and/or the bottom side projection has an annular flat portion with a width of 0.1 mm or more. Accordingly, the present invention provides a gasket excellent in properties such as sliding properties and resistance to liquid leakage without applying any sliding property improving agent that can adversely affect chemical liquids, for example silicone oil, to the sliding surface.

DESCRIPTION OF EMBODIMENTS

In the gasket of the present invention, the sliding surface of the gasket includes annular projections, and the gasket has polymer chains immobilized on at least part of its surface, wherein the annular projections include a first projection that is nearest to the top face, and a bottom side projection that is farthest from the top face, and the first projection and/or the bottom side projection has an annular flat portion with a width of 0.1 mm or more. Since polymer chains are immobilized on the surface of the gasket, and the sliding surface of the gasket includes annular projections, including a first projection and a bottom side projection, at least one of which has a certain annular flat portion, such a gasket has greatly enhanced sliding properties and can achieve both high sliding properties and high resistance to liquid leakage.

An example of a preferred embodiment of the present invention will be described below referring to drawings.

Figure 1:
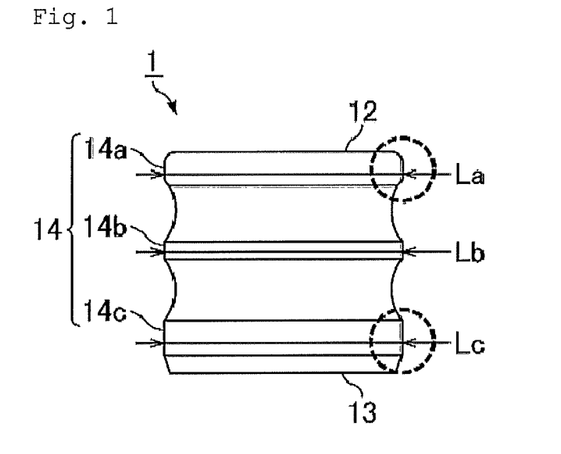
FIG. 1 is an exemplary side view showing a gasket base material onto which polymer chains are to be immobilized.
Figure 2:
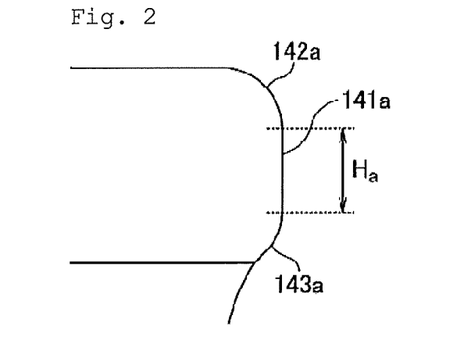
FIG. 2 is an exemplary partially enlarged view showing an annular flat portion of a first projection shown in FIG. 1.
Figure 3:
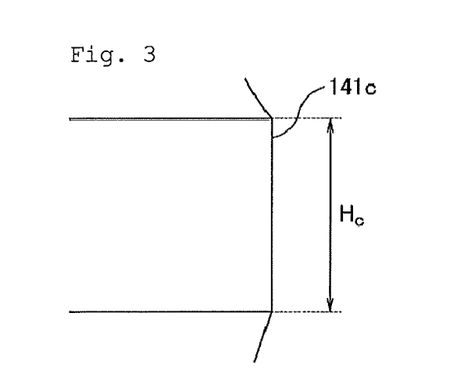
FIG. 3 is an exemplary partially enlarged view showing an annular flat portion of a bottom side projection shown in FIG. 1.

FIG. 1 is an exemplary side view showing a base material (gasket base material) onto which polymer chains are to be immobilized. FIGS. 2 and 3 are exemplary partially enlarged views showing annular flat portions of a first projection and a bottom side projection, respectively, shown in FIG. 1 (portions surrounded by circles).

The gasket of the present invention is used, for example, in a syringe that includes a barrel into which a liquid is to be injected, a plunger for pushing the liquid injected into the barrel, and a gasket attached to the tip of the plunger.

In the gasket, polymer chains (not shown) are immobilized on at least part of the surface of a gasket base material 1 shown in FIG. 1. In the straight cylindrical gasket base material 1 shown in FIG. 1, the circumference of a top face 12 on the liquid-contact side and the circumference of a bottom face 13 to be connected to the tip of a plunger are formed integrally with a sliding portion 14 (cylindrical portion) extending in the height direction (sliding direction).

The outer periphery of the sliding portion 14 includes: a first projection 14a that makes sliding contact with the inner periphery of the peripheral cylindrical portion of the barrel, at a position nearest to the top face 12; a bottom side projection 14c that makes sliding contact in the same manner, at a position farthest from the top face 12; and an intermediate projection 14b that makes sliding contact in the same manner, at a position between the projections 14a and 14c (in FIG. 1, the top face 12 is formed integrally with the first projection 14a).

As shown in FIG. 2 (a partially enlarged view of the first projection 14a) and FIG. 3 (a partially enlarged view of the bottom side projection 14c), the sliding contact surface of the first projection 14a includes an annular flat portion 141a (straight cylindrical portion) having a width Ha in the height direction (sliding direction) of the gasket base material 1, and the sliding contact surface of the bottom side projection 14c includes an annular flat portion 141c (straight cylindrical portion) having a width Hc in the same direction as above. Furthermore, in the example of FIG. 1, the intermediate projection 14b also includes an annular flat portion 141b (straight cylindrical portion, not shown) having a width Hb in the same direction as above. The annular flat portions each may not have a perfectly straight cylindrical shape. For use in syringes, for example, they may be in any form as long as they sufficiently make sliding contact with the inner periphery of the barrel so that resistance to liquid leakage can be ensured.

In order to simultaneously achieve sliding properties and resistance to liquid leakage, the width Hc of the annular flat portion 141c (bottom side annular flat portion) of the bottom side projection 14c is preferably greater than the width Ha of the annular flat portion 141a (first annular flat portion) of the first projection 14a.

In order to simultaneously achieve sliding properties and resistance to liquid leakage, the width Ha of the annular flat portion 141a (first annular flat portion) and the width Hc of the annular flat portion 141c (bottom side annular flat portion) are preferably both 0.1 mm or more. In particular, the first annular flat portion 141a preferably has a width Ha of 0.1 to 1.0 mm, more preferably 0.2 to 0.8 mm, still more preferably 0.2 to 0.4 mm. The bottom side annular flat portion 141c preferably has a width Hc of 0.2 mm or more, more preferably 0.4 mm or more, still more preferably 0.5 mm or more, but preferably 1.0 mm or less, more preferably 0.8 mm or less. The width Hb of the annular flat portion 141b (intermediate annular flat portion) of the intermediate projection 14b is preferably in the same range as the width Ha of the first annular flat portion.

In order to simultaneously achieve sliding properties and resistance to liquid leakage, the sliding contact surface of the first annular projection 14a preferably includes a curved surface portion (top side curved surface portion 142a) extending towards the top face from the first annular flat portion 141a, and a curved surface portion (bottom side curved surface portion 143a) extending towards the bottom face, in addition to the first annular flat portion 141a having a width Ha in the height direction of the gasket base material 1.

In particular, in order to simultaneously achieve sliding properties and resistance to liquid leakage, the bottom side curved surface portion 143a desirably has a greater curvature than the top side curved surface portion 142a in the first annular projection 14a. Specifically, the ratio of the curvature of the top side curved surface portion 142a to the curvature of the bottom side curved surface portion 143a is preferably 10/90 to 45/55, more preferably 20/80 to 45/55. Moreover, the bottom side curved surface portion 143a preferably has a curvature of 0.4 to 2.0, more preferably 0.4 to 1.0, still more preferably 0.6 to 1.0.

FIG. 1 shows an example where the intermediate projection 14b and the bottom side projection 14c have no curved surface portion; however, these projections may also have curved surface portions.

The gasket of the present invention includes a plurality of annular projections, and preferably three or more annular projections in order to simultaneously achieve sliding properties and resistance to liquid leakage. If the gasket includes three or more annular projections, one or more intermediate projections provided between the first projection and the bottom side projection desirably have a smaller outer diameter than the first projection and the bottom side projection. For example, in an embodiment including three annular projections as shown in FIG. 1, the intermediate projection 14b suitably has a smaller outer diameter than the first projection 14a and the bottom side projection 14c. The outer diameters of the first projection 14a, intermediate projection 14b, and bottom side projection 14c respectively correspond to the outer diameter La of the first annular flat portion 141a, the outer diameter Lb of the intermediate annular flat portion 141b, and the outer diameter Lc of the bottom side annular flat portion 141c.

In order to simultaneously achieve sliding properties and resistance to liquid leakage, the outer diameter(s) of the one or more intermediate projections between the first projection and the bottom side projection is/are preferably 96 to 99.5%, more preferably 97 to 98% of the outer diameter of the first projection.

In the straight cylindrical gasket base material 1, there is no particular restriction as to the other shapes of the top face 12 on the liquid-contact side, the bottom face 13 to be connected to the tip of a plunger, and the sliding portion 14 including the first projection 14a, the intermediate projection 14b, the bottom side projection 14c, and other cylindrical portions having smaller outer diameters than the projections 14a to 14c. They each may be any shape known in the gasket art.

As described above, the sliding surface of the gasket of the present invention includes annular projections, and polymer chains are immobilized on at least part of the surface of the gasket. The polymer chains are not particularly limited, and may be, for example, polymer chains formed by polymerizing a conventionally known monomer. The polymer chains may be immobilized by any method, including known methods, such as the "grafting from" method and the "grafting to (on)" method. In the grafting from method, graft polymerization of monomers is initiated from the surface. In the grafting to (on) method, polymer chains are reacted with and immobilized onto the surface.

Such a gasket of the present invention may be prepared, for example, by subjecting a gasket base material whose sliding surface includes annular projections to a surface modification method as described below.

The gasket of the present invention may be prepared by immobilizing polymer chains by a surface modification method that includes step 1 of forming polymerization initiation points A on a surface of a gasket base material, and step 2 of radically polymerizing a monomer, starting from the polymerization initiation points A, to grow polymer chains.

The step 1 includes forming polymerization initiation points A on a surface of a vulcanized rubber or a molded thermoplastic elastomer (gasket base material).

The vulcanized rubber or the thermoplastic elastomer may suitably contain a carbon atom adjacent to a double bond (i.e., allylic carbon atom).

Examples of rubber include diene rubbers such as styrene-butadiene rubber, polybutadiene rubber, polyisoprene rubber, natural rubber, and deproteinized natural rubber; butyl rubber and halogenated butyl rubber which have a degree of unsaturation of a few percent of isoprene units; and silicone rubber. In the case of butyl rubber or halogenated butyl rubber, it is preferably a rubber crosslinked by triazine because the amount of matter extracted from the vulcanized rubber is small. In such a case, the rubber may contain an acid acceptor. Suitable examples of the acid acceptor include hydrotalcite and magnesium carbonate.

If other rubbers are used, sulfur vulcanization is preferably performed. In such a case, compounding ingredients commonly used for sulfur vulcanization may be added, such as vulcanization accelerators, zinc oxide, filler, and silane coupling agents. Suitable examples of the filler include carbon black, silica, clay, talc, and calcium carbonate.

The vulcanization conditions for the rubber may be appropriately set. The rubber is preferably vulcanized at a temperature of 150° C. or higher, more preferably 170° C. or higher, still more preferably 175° C. or higher.

Examples of thermoplastic elastomers include polymer compounds that have rubber elasticity at room temperature owing to aggregates of plastic components (hard segments) serving as crosslinking points (e.g., thermoplastic elastomers (TPE) such as styrene-butadiene-styrene copolymer); and polymer compounds having rubber elasticity, obtained by mixing a thermoplastic component and a rubber component and dynamically crosslinking the mixture by a crosslinking agent (e.g., thermoplastic elastomers (TPV) such as polymer alloys containing a styrenic block copolymer or olefinic resin together with a crosslinked rubber component).

Other suitable thermoplastic elastomers include nylon, polyester, polyurethane, polypropylene, fluoroelastomers such as PTEF, and dynamically crosslinked thermoplastic elastomers thereof. Preferred among dynamically crosslinked thermoplastic elastomers are those obtained by dynamically crosslinking halogenated butyl rubber in a thermoplastic elastomer. The thermoplastic elastomer to be used is preferably nylon, polyurethane, polypropylene, styrene-isobutylene-styrene block copolymer (SIBS), or the like.

The polymerization initiation points A may be formed, for example, by adsorbing a photopolymerization initiator A onto a surface of a gasket base material. Examples of the photopolymerization initiator A include carbonyl compounds, organic sulfur compounds such as tetraethylthiuram disulfide, persulfides, redox compounds, azo compounds, diazo compounds, halogen compounds, and photoreductive pigments. Carbonyl compounds are especially preferred.

The carbonyl compound as the photopolymerization initiator A is preferably benzophenone or its derivative, and may suitably be a benzophenone compound represented by the following formula:

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary to tertiary amino group, a mercapto group, or a hydrocarbon group optionally containing an oxygen atom, a nitrogen atom, or a sulfur atom; and any two adjacent groups thereof may be joined to each other to form a cyclic structure together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Benzophenone, xanthone, and 9-fluorenone are particularly preferred because these compounds allow polymer brushes to be formed well.

Other suitable examples of the benzophenone compound include fluorobenzophenone compounds, such as 2,3,4,5,6-pentafluorobenzophenone and decafluorobenzophenone represented by the following formulas.

Thioxanthone compounds can also be suitably used as the photopolymerization initiator A because they provide a high polymerization rate and also can easily be adsorbed onto and/or reacted with rubber or the like. For example, compounds represented by the following formula can be suitably used.

In the formula, $R^{11}$ to $R^{14}$ and $R^{11'}$ to $R^{14'}$ are the same as or different from one another and each represent a hydrogen atom, a halogen atom, an alkyl group, a cyclic alkyl group, an aryl group, an alkenyl group, an alkoxy group, or an aryloxy group.

Examples of thioxanthone compounds represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are the compounds in which one or two, particularly two of the $R^{11}$ to $R^{14}$ and $R^{11'}$ to $R^{14'}$ are substituted with alkyl groups, and more preferred is 2,4-diethylthioxanthone.

The photopolymerization initiator A such as a benzophenone compound or thioxanthone compound can be adsorbed onto the surface of the gasket base material by conventionally known methods. For example, in the case of using a benzophenone compound or thioxanthone compound, the benzophenone or thioxanthone compound is dissolved in an organic solvent to prepare a solution, and a surface portion of the gasket base material to be modified is treated with this solution so that the compound is adsorbed onto the surface, optionally followed by evaporating off the organic solvent by drying, to form polymerization initiation points. The surface may be treated by any method that allows the solution of the benzophenone or thioxanthone compound to be brought into contact with the surface of the gasket base material. Suitable examples of the surface treatment method include application or spraying of the benzophenone or thioxanthone compound solution, and immersion into the solution. If only part of the surface needs to be modified, it is sufficient to adsorb the photopolymerization initiator A only onto such part of the surface. In this case, for example, application or spraying of the solution is suitable. Examples of the solvent include methanol, ethanol, acetone, benzene, toluene, methyl ethyl ketone, ethyl acetate, and THF. Acetone is preferred because it does not swell the gasket base material and it can be rapidly dried and evaporated off.

Moreover, after the portion onto which polymer chains are to be immobilized is surface treated with the benzophenone or thioxanthone compound solution so that the photopolymerization initiator A is adsorbed onto the surface, the surface of the gasket base material is preferably further irradiated with light so that the polymerization initiator A is chemically bonded to the surface. For example, the benzophenone or thioxanthone compound may be immobilized on the surface by irradiation with ultraviolet light having a wavelength of 300 to 450 nm, preferably 300 to 400 nm, more preferably 350 to 400 nm. During the step 1 and the immobilization, a hydrogen atom is abstracted from the rubber surface and a carbon atom on the rubber surface is then covalently bonded to the carbon atom in C=O of benzophenone while the abstracted hydrogen atom is bonded to the oxygen atom in C=O to form C—O—H, as shown in the scheme below. Moreover, since this hydrogen abstraction reaction selectively occurs on allylic hydrogen atoms in the gasket base material, the rubber preferably contains a butadiene or isoprene unit that contains an allylic hydrogen atom.

R: a hydrogen atom or a C1-C4 alkyl group

In particular, the polymerization initiation points A are preferably formed by treating the surface of the gasket base material with the photopolymerization initiator A so that the photopolymerization initiator A is adsorbed onto the surface, and then irradiating the treated surface with LED light having a wavelength of 300 to 450 nm. Particularly preferably, after the surface of the gasket base material is treated with the benzophenone or thioxanthone compound solution so that the photopolymerization initiator A is adsorbed, the treated surface is further irradiated with LED light having a wavelength of 300 to 450 nm so that the adsorbed photopolymerization initiator A is chemically bonded to the surface. Since light having a wavelength of less than 300 nm may break and damage the molecules in the gasket base material, light having a wavelength of 300 nm or more is preferably used. Light having a wavelength of 355 nm or more is more preferred in that such light causes only very small damage to the gasket base material. Also, since light having a wavelength of more than 450 nm is less likely to activate the polymerization initiator and thus less likely to allow the polymerization reaction to proceed, light having a wavelength of 450 nm or less is preferred. Light having a wavelength of 400 nm or less is more preferred for greater activation of the polymerization initiator. LED light having a wavelength of 355 to 380 nm is particularly suitable. LED light is suitable because it has a narrow band of wavelengths and thus does not have wavelengths other than the center wavelength. Mercury lamps or the like can produce the same effect as that of LED light if light having a wavelength of less than 300 nm is blocked using a filter.

The step 2 includes radically polymerizing a monomer, starting from the polymerization initiation points A, to grow polymer chains.

Non-limiting examples of the monomer include hydroxyalkyl (meth)acrylates such as hydroxyethyl (meth)acrylate and hydroxybutyl (meth)acrylate, (meth)acrylic acid, dimethyl (meth)acrylamide, diethyl (meth)acrylamide, isopropyl (meth)acrylamide, hydroxyethyl (meth)acrylamide, methoxymethyl (meth)acrylamide, (meth)acrylamide, methoxymethyl (meth)acrylate, (meth)acrylonitrile, and fluorine-containing monomers. These monomers may be used alone or in combinations of two or more. In particular, from the standpoint of cost efficiency, the monomer to be used in the step 2 is preferably (meth)acrylic acid, a hydroxyalkyl (meth)acrylate, dimethyl (meth)acrylamide, diethyl (meth)acrylamide, isopropyl (meth)acrylamide, hydroxyethyl (meth)acrylamide, methoxymethyl (meth)acrylamide, (meth)acrylamide, or methoxymethyl (meth)acrylate, more preferably (meth)acrylic acid or (meth)acrylamide, still more preferably acrylic acid or acrylamide.

Examples of fluorine-containing monomers include fluorine-containing (meth)acrylic-modified organosilicon compounds and cyclic siloxanes. Preferred among fluorine-containing monomers are monomers containing a perfluoropolyether group because they allow the effects of the present invention to be better achieved.

The fluorine-containing monomer may suitably be, for example, a fluorine-containing (meth)acrylic-modified organosilicon compound obtained by an addition reaction of (B) an unsaturated monocarboxylic acid containing a (meth)acrylic group with (A) a fluorine-containing epoxy-modified organosilicon compound represented by the following formula (1):

wherein $Rf^{11}$ represents a monovalent or divalent group having a molecular weight of 100 to 40,000 and containing a fluoroalkyl structure or a fluoropolyether structure; $Q^{11}$ represents a linking group having a siloxane structure, an unsubstituted or halogen-substituted silalkylene structure, a silarylene structure, or a combination of two or more thereof, each of which contains at least (a+b) silicon atoms and has a valency of (a+b), and $Q^{11}$ may have a cyclic structure; $Q^{12}$ represents a C1-20 divalent hydrocarbon group which may have a cyclic structure and may be interrupted by an ether linkage (—O—) or an ester linkage (—COO—); $R^{11}$ to $R^{13}$ each independently represent a hydrogen atom or a C1-10 monovalent hydrocarbon group, provided that a part or all of the hydrogen atoms of $R^{11}$ to $R^{13}$ may be replaced with a halogen atom, and $R^{11}$ and $R^{12}$ may be joined to each other to form a ring together with the carbon atoms to which they are attached; when $Rf^{11}$ is a monovalent group, a' and a represent 1 and an integer of 1 to 6, respectively, and when $Rf^{11}$ is a divalent group, a and a' represent 1 and 2, respectively; and b represents an integer of 1 to 20.

Regarding the fluorine-containing epoxy-modified organosilicon compound (A), specific examples of $Q^{11}$ in the formula (1) include groups having the structures represented by the following formulas.

In the formulas, a and b are as defined above and each are preferably an integer of 1 to 4. Moreover, a+b is preferably an integer of 3 to 5. A unit repeated a times and a unit repeated b times are randomly arranged. The bond represented by the broken line in each of the unit repeated a times and the unit repeated b times is attached to $Rf^{11}$ or the group represented by the following formula:

wherein $Q^{11}$ and $R^{11}$ to $R^{13}$ are as defined above.

The divalent hydrocarbon group for $Q^{12}$ in the formula (1) preferably has 2 to 15 carbon atoms. Specific examples of the structure of $Q^{12}$ include —CH$_2$CH$_2$—, —CH$_2$CH(CH$_3$)—, and —CH$_2$CH$_2$CH$_2$OCH$_2$—.

The monovalent hydrocarbon group for $R^{11}$ to $R^{13}$ preferably has 1 to 8 carbon atoms. Specific examples of $R^{11}$ to $R^{13}$ include a hydrogen atom, alkyl groups such as a methyl group, an ethyl group, and a propyl group, and cycloalkyl groups such as a cyclopentyl group and a cyclohexyl group.

Examples of the group containing a combination of $R^{11}$ to $R^{13}$ and $Q^{12}$ represented by the above formula include the following groups.

$Rf^{11}$ in the formula (1) preferably has a molecular weight of 500 to 20,000. Moreover, $Rf^{11}$ suitably contains 1 to 500, preferably 2 to 400, more preferably 4 to 200 repeating units of the formula: —C$_i$F$_{2i}$O— wherein i in each unit independently represents an integer of 1 to 6. In the present invention, molecular weight refers to number average molecular weight calculated from the ratio between the chain end structure and the backbone structure as determined by $^1$H-NMR and $^{19}$F-NMR.

Examples of $Rf^{11}$ in the formula (1) include groups represented by the following formula (3):

wherein $Rf^{11}$ represents a divalent perfluoropolyether group having a molecular weight of 300 to 30,000 which may be internally branched; $Q^{13}$ represents a divalent organic group which may contain an oxygen atom, a nitrogen atom, a fluorine atom or a silicon atom and may contain a cyclic structure or an unsaturated bond; $Q_f^{11}$ represents $Q^{13}$ or a fluorine atom; T represents a linking group represented by the following formula (4):

(4)

wherein $R^{11}$ to $R^{13}$, $Q^{12}$, a, and b are as defined in the formula (1), and $Q^{14}$ represents a linking group having a siloxane structure, an unsubstituted or halogen-substituted silalkylene structure, a silarylene structure, or a combination of two or more thereof, each of which contains at least (a+b) silicon atoms and has a valency of (a+b); and v represents an integer of 0 to 5, provided that v is 0 when $Q_f^{11}$ is a fluorine atom.

$Rf^{11}$ in the formula (3) preferably has a molecular weight of 500 to 20,000. Specific examples of $Rf^{11}$ include divalent perfluoropolyether groups represented by the following formulas:

wherein Ys each independently represent a fluorine atom or $CF_3$ group; r represents an integer of 2 to 6; m and n each represent an integer of 0 to 200, preferably 0 to 100, provided that m+n is an integer of 2 to 200, preferably 3 to 150; s represents an integer of 0 to 6; and the repeating units may be randomly linked, and wherein j represents an integer of 1 to 3, and k represents an integer of 1 to 200, preferably 1 to 60.

Examples of $Q^{13}$ in the formula (3) include the following groups:

wherein Ph represents a phenyl group.

In the formula (1), when $Rf^{11}$ is a monovalent group, a is preferably an integer of 1 to 3. The b is preferably an integer of 1 to 6, and a+b is preferably an integer of 3 to 6.

Specific examples of $Rf^{11}$ in the formula (1) include the following groups:

wherein m, n, r, and s are as defined above.

Specific examples of the fluorine-containing epoxy-modified organosilicon compound (A) include the following compounds:

-continued wherein j, m, and n are as defined above, and b' is an integer of 1 to 8.

These fluorine-containing epoxy-modified organosilicon compounds may be used alone or in combinations of two or more.

The unsaturated monocarboxylic acid (B) containing a (meth)acrylic group is suitably acrylic acid or methacrylic acid although it may be one in which a part of the hydrogen atoms is halogenated with a halogen atom (e.g. chlorine, fluorine), such as 2-chloroacrylic acid, 2-(trifluoromethyl) acrylic acid, or 2,3,3-trifluoroacrylic acid. Furthermore, these carboxylic acids protected by an allyl group, a silyl group, or the like may optionally be used. The unsaturated monocarboxylic acids may be used alone or in combinations of two or more.

The fluorine-containing (meth)acrylic-modified organosilicon compound is obtained by reacting the epoxy group of the fluorine-containing epoxy-modified organosilicon compound (A) with the carboxyl group of the unsaturated monocarboxylic acid (B) containing a (meth)acrylic group by a conventionally known method. Specific examples of the fluorine-containing (meth)acrylic-modified organosilicon compound include the following compounds:

-continued wherein j, m, n, and b' are as defined above.

The fluorine-containing monomer may suitably be a mixture of a fluorine-containing epoxy-modified organosilicon compound as specifically exemplified above and a fluorine-containing (meth)acrylic-modified organosilicon compound as specifically exemplified above. It is particularly preferably a mixture of a fluorine-containing epoxy-modified organosilicon compound represented by the formula below and a fluorine-containing (meth)acrylic-modified organosilicon compound represented by the formula below:

wherein $b'_1+b'_2$ is 2 to 6.5, and $Rf^{12}$ is a group represented by the following formula:

wherein $n_1$ is 2 to 100. In such a case, the effects of the present invention can be better achieved.

The fluorine-containing monomer may also be a polyfunctional (meth)acrylate compound containing per molecule three or more fluorine atoms and three or more silicon atoms and including a cyclic siloxane represented by the following formula:

$$(Rf^{21}R^{21}SiO)(R^4R^{21}SiO)_h$$

wherein $R^{21}$ represents a hydrogen atom, a methyl group, an ethyl group, a propyl group, or a phenyl group; $Rf^{21}$ represents a fluorine-containing organic group; $R^4$ represents a (meth)acrylic group-containing organic group; and h satisfies $h \geq 2$.

$Rf^{21}$ in the polyfunctional (meth)acrylate compound may be a group represented by $C_tF_{2t+1}(CH_2)_u$— wherein t represents an integer of 1 to 8, and u represents an integer of 2 to 10, or may be a perfluoropolyether-substituted alkyl group. Specific examples include $CF_3C_2H_4$—, $C_4F_9C_2H_4$—, $C_4F_9C_3H_6$—, $C_8F_{17}C_2H_4$—, $C_8F_{17}C_3H_6$—, $C_3F_7C(CF_3)_2$ $C_3H_6$—, $C_3F_7OC(CF_3)FCF_2OCF_2CF_2C_3H_6$—, $C_3F_7OC(CF_3)$ $FCF_2OC(CF_3)$ $FC_3H_6$—, and $CF_3CF_2CF_2OC(CF_3)$ $FCF_2OC(CF_3)FCONHC_3H_6$—.

Specific examples of $R^A$ include $CH_2=CHCOO-$, $CH_2=C(CH_3)COO-$, $CH_2=CHCOOC_3H_6-$, $CH_2=C(CH_3)COOC_3H_6-$, $CH_2=CHCOOC_2H_4O-$, and $CH_2=C(CH_3)COOC_2H_4O-$. Moreover, $R^A$ is preferably bound to the silicon atom by a Si—O—C bond. The h preferably satisfies $3 \le h \le 5$.

The polyfunctional (meth)acrylate compound contains per molecule three or more fluorine atoms and three or more silicon atoms, and preferably contains per molecule 3 to 17 fluorine atoms and 3 to 8 silicon atoms.

Specific examples of the polyfunctional (meth)acrylate compound include compounds represented by the following formulas.

The fluorine-containing monomer is also preferably characterized by an infrared absorption spectrum having absorption peaks at about 1045 cm$^{-1}$, about 1180 cm$^{-1}$, about 806 cm$^{-1}$, about 1720 cm$^{-1}$, about 1532 cm$^{-1}$, and about 3350 cm$^{-1}$. In particular, it is suitably characterized by an infrared absorption spectrum having strong absorption peaks at about 1045 cm$^{-1}$ and about 1180 cm$^{-1}$, absorption peaks at about 806 cm$^{-1}$ and about 1720 cm$^{-1}$, a weak absorption peak at about 1532 cm$^{-1}$, and a broad weak absorption peak at about 3350 cm$^{-1}$. In such a case, polymer chains having better properties including better sliding properties can be formed.

Moreover, the fluorine-containing monomer is preferably characterized by a $^{13}$C NMR spectrum in chloroform-d (deuterated chloroform) having signals at chemical shifts of about 13.01, 14.63, 23.04, 40.13, 50.65, 63.54, 68.97, 73.76, 76.74, 77.06, 77.38, 113.21, 114.11, 116.96, 117.72, 118.47, 128.06, 131.38, 156.46, and 166.02 ppm.

Furthermore, the fluorine-containing monomer is preferably characterized by a $^1$H NMR spectrum in chloroform-d (deuterated chloroform) having signals at chemical shifts of about 3.40, 3.41, 3.49, 3.60, 5.26, 5.58, 6.12, 6.14, 6.40, 6.42, and 6.46 ppm.

In the step 2, the monomer may be radically polymerized as follows. The (liquid) monomer or a solution of the monomer is applied (sprayed) to the surface of the gasket base material to which a benzophenone compound, a thioxanthone compound, or the like is adsorbed or covalently bonded. Alternatively, the gasket base material is immersed in the (liquid) monomer or a solution thereof. Then, the gasket base material is irradiated with light, such as ultraviolet light, to allow the radical polymerization (photoradical polymerization) to proceed. Thus, polymer chains can be grown on the surface of the gasket base material. In another method, after the application, the surface may be covered with a transparent sheet of glass, PET, polycarbonate, or the like, followed by irradiating the covered surface with light, such as ultraviolet light, to allow the radical polymerization (photoradical polymerization) to proceed. Thus, polymer chains can be grown on the surface of the gasket base material.

Moreover, the amount of the radically polymerizable monomer may be appropriately set depending on, for example, the length of polymer chains to be formed, or the properties to be provided by the chains.

The solvent for application (spraying), the method for application (spraying), the method for immersion, the conditions for irradiation, and the like may be conventionally known materials or methods. The solution of the radically polymerizable monomer may be an aqueous solution, or a solution in an organic solvent that does not dissolve the photopolymerization initiator (e.g. benzophenone compound or thioxanthone compound) used. Furthermore, the (liquid) radically polymerizable monomer or a solution thereof may contain a known polymerization inhibitor such as 4-methylphenol.

The radical polymerization of the monomer is allowed to proceed by light irradiation after the application of the (liquid) monomer or a solution thereof or after the immersion in the (liquid) monomer or a solution thereof. Here, UV light sources with an emission wavelength mainly in the ultraviolet region, such as high-pressure mercury lamps, metal halide lamps, and LED lamps, can be suitably used. The light dose may be appropriately determined in view of polymerization time and uniform reaction progress. Moreover, in order to prevent inhibition of polymerization due to active gas such as oxygen in the reaction vessel, oxygen is preferably removed from the reaction vessel and the reaction solution during or before the light irradiation. For this purpose, appropriate operations may be performed. For example, an inert gas such as nitrogen gas or argon gas is inserted into the reaction vessel and the reaction solution to discharge active gas such as oxygen from the reaction system and thereby replace the atmosphere in the reaction system with the inert gas. Or the reaction vessel is evacuated to remove oxygen. Also, in order to prevent inhibition of the reaction due to oxygen or the like, for example, a measure may appropriately be taken in which a UV light source is disposed so that no air layer (oxygen content: 15% or higher) exists between the reaction vessel made of glass, plastics or the like and the reaction solution or the gasket base material.

In the case of irradiation with ultraviolet light, the ultraviolet light preferably has a wavelength of 300 to 450 nm, more preferably 300 to 400 nm. Such light allows polymer chains to be formed well on the surface of the gasket base material. The light source may be a high-pressure mercury lamp, an LED with a center wavelength of 365 nm, an LED with a center wavelength of 375 nm, or the like. In particular, preferred is irradiation with LED light having a wavelength of 300 to 450 nm, more preferably LED light having a wavelength of 355 to 380 nm. LEDs or the like having a center wavelength of 365 nm, which is close to the excitation wavelength of benzophenone, 366 nm, are particularly preferred in view of efficiency.

The surface modification method may include step 3 of further extending the polymer chains grown in the step 2, or immobilizing different polymer chains onto the polymer chains grown in the step 2. The step 3 is not particularly limited as long as it is a step of further extending or immobilizing polymer chains. For example, the step 3 may include step 3-1 of forming polymerization initiation points B on surfaces of the polymer chains grown in the step 2, and step 3-2 of radically polymerizing a monomer, starting from the polymerization initiation points B, to grow polymer chains.

In the step 3-1, the polymerization initiation points B may be formed by the same techniques as those mentioned in the step 1, such as by additionally adsorbing a photopolymerization initiator B onto surfaces of the formed polymer chains, optionally followed by chemically bonding the photopolymerization initiator B to the surface. The photopolymerization initiator B may be as mentioned for the photopolymerization initiator A.

In the step 3-2, a monomer is radically polymerized starting from the polymerization initiation points B, to grow polymer chains.

The monomer to be used in the step 3-2 may be as mentioned for the monomer used in the step 2. In particular, the monomer is preferably (meth)acrylonitrile or a fluorine-containing monomer, more preferably a fluorine-containing monomer, because they provide excellent resistance to liquid leakage and excellent sliding properties.

In the step 3-2, the monomer may be radically polymerized as mentioned for the method of radically polymerizing a monomer in the step 2.

In the step 3, a cycle of the steps 3-1 and 3-2 may further be repeated. In this case, the polymer chains that have been chain extended in the steps 3-1 and 3-2 are further extended with polymer chains.

The gasket of the present invention can also be prepared by immobilizing polymer chains by a surface modification method that includes step I of radically polymerizing a monomer in the presence of a photopolymerization initiator A on a surface of a gasket base material to grow polymer chains. The surface modification method may include step II of further extending the polymer chains grown in the step I, or immobilizing different polymer chains onto the polymer chains grown in the step I. In the step II, the extension or immobilization process may be repeated. In such a case, the polymer chains that have been chain extended are further chain extended.

For example, the step I may be carried out by contacting a photopolymerization initiator A and a monomer with a surface of a gasket base material, followed by irradiation with LED light having a wavelength of 300 to 450 nm to form polymerization initiation points A from the photopolymerization initiator A while radically polymerizing the monomer, starting from the polymerization initiation points A, to grow polymer chains; and the step II may be carried out by contacting a photopolymerization initiator B and a monomer with surfaces of the polymer chains formed in the step I, followed by irradiation with LED light having a wavelength of 300 to 450 nm to form polymerization initiation points B from the photopolymerization initiator B while radically polymerizing the monomer, starting from the polymerization initiation points B, to grow polymer chains.

In the step I and step II, the monomers may be radically polymerized as follows. The (liquid) monomer or a solution of the monomer, which contains a photopolymerization initiator A or B, e.g. a benzophenone compound or a thioxanthone compound, is applied (sprayed) to a surface of a gasket base material or to the gasket base material on which polymer chains are formed in the step I. Alternatively, a gasket base material or the gasket base material on which polymer chains are formed in the step I is immersed in the (liquid) monomer or a solution thereof, which contains a photopolymerization initiator A or B. Then, the gasket base material is irradiated with light, such as ultraviolet light, to allow the radical polymerization (photoradical polymerization) of the monomer to proceed. Thus, polymer chains can be grown or extended on the surface of the gasket base material. In another method, for example, the surface may be covered with the above-mentioned transparent sheet of glass, PET, polycarbonate, or the like, followed by irradiating the covered surface with light such as ultraviolet light. Here, a reducing agent or an antioxidant may be added. The solvent for application (spraying), the method for application (spraying), the method for immersion, the conditions for irradiation, and the like may be the same materials or methods as mentioned above.

The polymer chains finally formed by the surface modification method preferably have a polymerization degree of 20 to 200000, more preferably 350 to 50000.

The entire length of the finally formed polymer chain is preferably 10 to 50000 nm, more preferably 100 to 50000 nm, still more preferably 500 to 10000 nm. If the entire length is shorter than 10 nm, good sliding properties tend not to be achieved. If the entire length is longer than 50000 nm, a further improvement in sliding properties cannot be expected while the cost of raw materials tends to increase due to the use of the expensive monomer. In addition, surface patterns generated by the surface treatment tend to be visible to the naked eyes and thereby spoil the appearance and decrease sealing properties.

In the step 2, step 3, step I, and step II, two or more kinds of monomers may simultaneously be radically polymerized starting from the polymerization initiation points A or B. Furthermore, multiple kinds of polymer chains may be grown on the surface of the gasket base material. In the surface modification method, the polymer chains may be crosslinked to one another. In this case, the polymer chains may be crosslinked to one another by ionic crosslinking, crosslinking by a hydrophilic group containing an oxygen atom, or crosslinking by a halogen group such as iodine. Crosslinking by UV irradiation or electron beam irradiation may be employed.

The polymer chains may be provided on at least part of or the entire surface of the gasket base material. In particular, in view of sliding properties and the like, preferably at least the sliding surface of the gasket base material is modified.

EXAMPLES

Examples 1 to 9

A gasket base material having a shape specified in Table 1 (chlorobutyl rubber (degree of unsaturation: 1 to 2%) containing isoprene units, crosslinked by triazine (vulcanized at 180° C. for 10 minutes)) was immersed in a 3 wt % solution of benzophenone in acetone for 5 minutes so that benzophenone was adsorbed onto the surface of the gasket base material, followed by drying.

The dried gasket base material was immersed in a 2.5 M acrylamide aqueous solution in a glass reaction vessel. Then, the gasket base material was irradiated with LED-UV light having a wavelength of 365 nm for 150 minutes to cause radical polymerization, whereby polymer chains were grown on the rubber surface. Thus, a desired gasket was prepared.

Example 10

A gasket base material having a shape specified in Table 1 (chlorobutyl rubber (degree of unsaturation: 1 to 2%) containing isoprene units, crosslinked by triazine (vulcanized at 180° C. for 10 minutes)) was immersed in a 3 wt % solution of benzophenone in acetone so that benzophenone was adsorbed onto the surface of the gasket base material, followed by drying.

The dried gasket base material was immersed in a 2.5 M acrylamide aqueous solution in a glass reaction vessel. Then, the gasket base material was irradiated with LED-UV light having a wavelength of 365 nm for 150 minutes to cause radical polymerization, whereby polymer chains were grown on the rubber surface. Thereafter, the surface was washed with water and dried.

Next, the dried gasket was again immersed in a 3 wt % solution of benzophenone in acetone for 5 minutes so that benzophenone was adsorbed onto the surfaces of the polymer chains, followed by drying.

Further, a fluorine-containing monomer liquid (20 wt % dilution in ethanol of KY-1203 (produced by Shin-Etsu Chemical Co., Ltd., a mixture of a fluorine-containing epoxy-modified organosilicon compound represented by the formula below and a fluorine-containing (meth)acrylic-modified organosilicon compound represented by the formula below) was applied to the surface of the dried gasket. Then, the surface was irradiated with LED-UV light having a wavelength of 365 nm for 10 minutes to cause radical polymerization, whereby the polymer chains were extended. Thus, a desired gasket was prepared.

In the formulas, $b'_1+b'_2$ is 2 to 6.5, and $Rf'^{12}$ is the following group:

wherein $n_1$ is 2 to 100.

Example 11

A gasket base material having a shape specified in Table 1 (chlorobutyl rubber (degree of unsaturation: 1 to 2%) containing isoprene units, crosslinked by triazine (vulcanized at 180° C. for 10 minutes)) was immersed in a 3 wt % solution of benzophenone in acetone so that benzophenone was adsorbed onto the surface of the gasket base material, followed by drying.

The dried gasket base material was immersed in a 2.5 M mixed aqueous solution of acrylamide and acrylic acid (acrylamide:acrylic acid=75:25) in a glass reaction vessel. Then, the gasket base material was irradiated with LED-UV light having a wavelength of 365 nm for 150 minutes to cause radical polymerization, whereby polymer chains were grown on the rubber surface. Thereafter, the surface was washed with water and dried.

Next, the dried gasket was again immersed in a 3 wt % solution of benzophenone in acetone for 5 minutes so that benzophenone was adsorbed onto the surfaces of the polymer chains, followed by drying.

Further, a fluorine-containing monomer liquid (20 wt % dilution in ethanol of KY-1203 (produced by Shin-Etsu Chemical Co., Ltd., a mixture of a fluorine-containing epoxy-modified organosilicon compound represented by the formula below and a fluorine-containing (meth)acrylic-modified organosilicon compound represented by the formula below) was applied to the surface of the dried gasket. Then, the surface was irradiated with LED-UV light having a wavelength of 365 nm for 10 minutes to cause radical polymerization, whereby the polymer chains were extended. Thus, a desired gasket was prepared.

Comparative Example 1

A vulcanized rubber gasket (vulcanized at 180° C. for 10 minutes), which was prepared by crosslinking chlorobutyl rubber (degree of unsaturation: 1 to 2%) containing isoprene units by triazine, was used as it was.

Comparative Example 2

A gasket base material having a shape specified in Table 1 (chlorobutyl rubber (degree of unsaturation: 1 to 2%) containing isoprene units, crosslinked by triazine (vulcanized at 180° C. for 10 minutes)) was immersed in a 3 wt % solution of benzophenone in acetone for 5 minutes so that benzophenone was adsorbed onto the surface of the gasket base material, followed by drying.

The dried gasket base material was immersed in a 2.5 M acrylamide aqueous solution in a glass reaction vessel. Then, the gasket base material was irradiated with LED-UV light having a wavelength of 365 nm for 150 minutes to cause radical polymerization, whereby polymer chains were grown on the rubber surface. Thus, a desired gasket was prepared.

The surface-modified elastic bodies prepared in the examples and comparative examples were evaluated by the methods mentioned below.

(Length of Polymer Chain)

To determine the length of the polymer chain formed on the surface of the gasket, a cross section of the gasket having polymer chains formed thereon was measured with an SEM at an accelerating voltage of 15 kV and a magnification of 1000 times. The thickness of the polymer layer photographed was determined and used as the length of the polymer chain.

(Friction Resistance)

To determine the friction resistance of the surface of the gasket, the vulcanized rubber gaskets prepared in the examples and comparative examples were each inserted into a COP resin barrel of a syringe and then pushed towards the end of the barrel (push rate: 30 ram/min) using a tensile tester while friction resistance was measured. The values of the examples are expressed as a friction resistance index using the equation below, with the friction resistance of Comparative Example 1 being set equal to 100. A lower index indicates a lower friction resistance.

(Friction resistance index)=(Friction resistance of each example)/(Friction resistance of Comparative Example 1)×100

(Resistance to Liquid Leakage)

The vulcanized rubber gaskets prepared in the examples and comparative examples were each inserted into a COP resin barrel of a syringe. A solution of red food coloring in water was introduced into the barrel, and the barrel was sealed with a cap. After two-week storage at 40° C., the barrel was visually observed for liquid leakage.

TABLE 1

| | Outer diameter of first projection mm | Width of flat portion of first projection mm | Outer diameter of intermediate projection (second projection) mm | Width of flat portion of intermediate projection (second projection) mm | Outer diameter of bottom side projection (third projection) mm | Width of flat portion of bottom side projection (third projection) mm | Outer diameter ratio of intermediate projection to first projection % |
|---|---|---|---|---|---|---|---|
| Ex. 1 | 6.7 | 0.1 | 6.7 | 0.1 | 6.7 | 0.1 | 100.0 |
| Ex. 2 | 6.7 | 0.2 | 6.7 | 0.2 | 6.7 | 0.2 | 100.0 |
| Ex. 3 | 6.7 | 0.5 | 6.7 | 0.5 | 6.7 | 0.5 | 100.0 |
| Ex. 4 | 6.7 | 0.8 | 6.7 | 0.8 | 6.7 | 0.8 | 100.0 |
| Ex. 5 | 6.7 | 0.2 | 6.7 | 0.2 | 6.7 | 0.5 | 100.0 |
| Ex. 6 | 6.7 | 0.2 | 6.45 | 0.2 | 6.7 | 0.5 | 96.3 |
| Ex. 7 | 6.7 | 0.2 | 6.55 | 0.2 | 6.7 | 0.5 | 97.8 |
| Ex. 8 | 6.7 | 0.2 | 6.55 | 0.2 | 6.7 | 0.5 | 97.8 |
| Ex. 9 | 6.7 | 0.2 | 6.55 | 0.2 | 6.7 | 0.5 | 97.8 |
| Ex. 10 | 6.7 | 0.2 | 6.55 | 0.2 | 6.7 | 0.5 | 97.8 |
| Ex. 11 | 6.7 | 0.2 | 6.55 | 0.2 | 6.7 | 0.5 | 97.8 |
| Com. Ex. 1 | 6.7 | 0 | 6.7 | 0 | 6.7 | 0 | 100.0 |
| Com. Ex. 2 | 6.7 | 0 | 6.7 | 0 | 6.7 | 0 | 100.0 |

| | Curvature of top side curved surface portion | Curvature of bottom side curved surface portion | First layer monomer | Second layer monomer | Length of polymer chain nm | Friction resistance index | Resistance to liquid leakage |
|---|---|---|---|---|---|---|---|
| Ex. 1 | 0.3 | 0.3 | Acrylamide | None | 8000 | 2.5 | No problem |
| Ex. 2 | 0.3 | 0.3 | Acrylamide | None | 8000 | 2.56 | No problem |
| Ex. 3 | 0.3 | 0.3 | Acrylamide | None | 7500 | 2.75 | No problem |
| Ex. 4 | 0.3 | 0.3 | Acrylamide | None | 8500 | 2.94 | No problem |
| Ex. 5 | 0.3 | 0.3 | Acrylamide | None | 8500 | 2.6 | No problem |
| Ex. 6 | 0.3 | 0.3 | Acrylamide | None | 7500 | 2.45 | No problem |
| Ex. 7 | 0.3 | 0.3 | Acrylamide | None | 8000 | 2.47 | No problem |
| Ex. 8 | 0.3 | 0.4 | Acrylamide | None | 7500 | 2.46 | No problem |
| Ex. 9 | 0.3 | 0.8 | Acrylamide | None | 7500 | 2.45 | No problem |
| Ex. 10 | 0.3 | 0.4 | Acrylamide | KY1203 | 9000 | 1.75 | No problem |
| Ex. 11 | 0.3 | 0.4 | Acrylamide/ | KY1203 | 7500 | 1.54 | No problem |
| Com. Ex. 1 | 0.3 | 0.3 | No graft polymer | | — | 100 | No problem |
| Com. Ex. 2 | 0.3 | 0.3 | Acrylamide | None | 8000 | 2.48 | Partially exuded |

Table 1 demonstrates that the surfaces of the gaskets prepared in the examples exhibited greatly reduced friction resistances and good sliding properties. Also, the results of Comparative Example 2 and the examples demonstrate that the gaskets having specific shapes showed better resistance to liquid leakage.

Thus, when these gaskets are used for syringe plungers, they provide sufficient resistance to liquid leakage while reducing the friction of the plunger with the syringe barrel, and therefore they enable easy and accurate treatment with syringes. Moreover, they have a small difference between static and kinetic coefficients of friction, and therefore the start of pushing the plunger and the subsequent inward movements of the plunger can be smoothly carried out without pulsation. Furthermore, if polymer chains are formed on the inner surface of a syringe barrel made of a thermoplastic elastomer, treatment with the syringe can be readily performed, similarly as described above.

REFERENCE SIGNS LIST

1: Gasket base material
12: Top face
13: Bottom face
14: Sliding portion
14a: First projection
14b: Intermediate projection
14c: Bottom side projection
141a: Annular flat portion of first projection (first annular flat portion)
141c: Annular flat portion of bottom side projection (bottom side annular flat portion)
La: Outer diameter of first annular flat portion
Lb: Outer diameter of intermediate annular flat portion
Lc: Outer diameter of bottom side annular flat portion
Ha: Width of annular flat portion of first projection
Hc: Width of annular flat portion of bottom side projection
142a: Top side curved surface portion
143a: Bottom side curved surface portion

The invention claimed is:

1. A gasket whose sliding surface comprises annular projections, the gasket having polymer chains immobilized on at least part of its surface,
   the annular projections including a first projection that is nearest to a top face, and a bottom side projection that is farthest from the top face,
   at least one of the first projection or the bottom side projection having an annular flat portion with a width of 0.1 mm or more,
   wherein a curved surface portion is provided on top and bottom sides of the first projection, and
   wherein the curved surface portion on the bottom side has a greater curvature than the curved surface portion on the top side.

2. The gasket according to claim 1,
   wherein the bottom side projection has an annular flat portion which is wider than that of the first projection.

3. The gasket according to claim 1,
   wherein the bottom side projection has an annular flat portion with a width of 0.4 mm or more.

4. The gasket according to claim 1,
   wherein the gasket comprises three or more annular projections,
   the annular projections include an intermediate projection between the first projection and the bottom side projection, and
   the intermediate projection has a smaller outer diameter than the first projection and the bottom side projection.

5. The gasket according to claim 4,
   wherein the outer diameter of the intermediate projection is 96 to 99.5% of the outer diameter of the first projection.

6. The gasket according to claim 1,
   wherein the curved surface portion on the bottom side has a curvature of 0.4 to 2.0.

7. The gasket according to claim 1,
   wherein the polymer chains are immobilized by a surface modification method comprising:
   step 1 of forming polymerization initiation points A on a surface of a gasket base material; and
   step 2 of radically polymerizing a monomer, starting from the polymerization initiation points A, to grow polymer chains.

8. The gasket according to claim 7,
   wherein the surface modification method comprises
   step 3 of further extending the polymer chains grown in the step 2, or immobilizing different polymer chains onto the polymer chains grown in the step 2.

9. The gasket according to claim 7,
   wherein the step 1 comprises adsorbing a photopolymerization initiator A onto a surface of a gasket base material, optionally followed by irradiation with LED light having a wavelength of 300 to 450 nm, to form polymerization initiation points A from the photopolymerization initiator A on the surface.

10. The gasket according to claim 7,
    wherein the step 2 comprises radically polymerizing a monomer, starting from the polymerization initiation points A, by irradiation with LED light having a wavelength of 300 to 450 nm to grow polymer chains.

11. The gasket according to claim 1,
    wherein the polymer chains are immobilized by a surface modification method comprising
    step I of radically polymerizing a monomer in the presence of a photopolymerization initiator A on a surface of a gasket base material to grow polymer chains.

12. The gasket according to claim 11,
    wherein the surface modification method comprises
    step II of further extending the polymer chains grown in the step I, or immobilizing different polymer chains onto the polymer chains grown in the step I.

13. The gasket according to claim 11,
    wherein the step I comprises radically polymerizing a monomer by irradiation with LED light having a wavelength of 300 to 450 nm to grow polymer chains.

14. The gasket according to claim 1,
    wherein a length of the polymer chain is 10 to 50000 nm.

* * * * *